(12) United States Patent
Barker et al.

(10) Patent No.: US 7,704,534 B2
(45) Date of Patent: *Apr. 27, 2010

(54) CONTINUOUS PROCESS FOR PRODUCTION OF OIL SEED PROTEIN ISOLATE

(75) Inventors: Larry D. Barker, Winnipeg (CA); Brent Everett Green, Winnipeg (CA); Lei Xu, Ottawa (CA)

(73) Assignee: Burcon NutraScience (MB) Corp., Winnipeg, Manitoba (CA)

(*) Notice: Subject to any disclaimer, the term of this patent is extended or adjusted under 35 U.S.C. 154(b) by 0 days.

This patent is subject to a terminal disclaimer.

(21) Appl. No.: 12/230,199

(22) Filed: Aug. 26, 2008

(65) Prior Publication Data

US 2008/0319171 A1 Dec. 25, 2008

Related U.S. Application Data

(63) Continuation of application No. 10/298,678, filed on Feb. 14, 2003, now abandoned.

(60) Provisional application No. 60/383,809, filed on May 30, 2002, provisional application No. 60/331,646, filed on Nov. 20, 2001.

(51) Int. Cl.
*A61K 36/00* (2006.01)
*A61K 47/00* (2006.01)
*A61K 9/00* (2006.01)
*A01K 65/00* (2006.01)

(52) U.S. Cl. .................... 424/776; 424/725; 424/400; 424/439

(58) Field of Classification Search ............... None
See application file for complete search history.

(56) References Cited

U.S. PATENT DOCUMENTS

| 4,158,656 A | * | 6/1979 | Jones et al. ............. 530/377 |
| 4,169,090 A | | 9/1979 | Murray |
| 4,208,323 A | | 6/1980 | Murray |
| 4,285,862 A | | 8/1981 | Murray |
| 4,420,425 A | | 12/1983 | Lawhon |
| 4,704,289 A | | 11/1987 | Scheide |
| 5,503,832 A | | 4/1996 | De Stoutz |
| 5,844,086 A | * | 12/1998 | Murray ............. 530/377 |
| 6,005,076 A | * | 12/1999 | Murray ............. 530/377 |
| 2004/0034200 A1 | | 2/2004 | Logie |

FOREIGN PATENT DOCUMENTS

| DE | 2322462 | 11/1974 |
| DE | 247835 | 7/1987 |
| DE | 10035292 A | 2/2002 |
| JP | 5043597 A | 2/1993 |

OTHER PUBLICATIONS

Murray et al. "Rapeseed: a potential global source of high quality plant protein", (Apr. 2001), pp. 30-34 (Asia Pacific Food Industry, Apr. 2001).
XP-002246020 (Feb. 23, 1993), abstract.
James R. Witcox et al "Interrelationships among Seed Quality Attributes in Soybean" (Published in Corp. Sci. 41:11-14 (2001)).

* cited by examiner

*Primary Examiner*—Christopher R Tate
*Assistant Examiner*—Randall Winston
(74) *Attorney, Agent, or Firm*—Michael I. Stewart; Sim & McBurney

(57) ABSTRACT

Oil seed protein isolates, particularly canola protein isolate, are produced continuously from oil seed meals, preferably at a high purity level of at least about 100 wt % (Nx 6.25), by a process wherein oil seed protein is continuously extracted from oil seed meal, the resulting protein solution is continuously concentrated, preferably to a protein content of at least about 200 g/L, and the concentrated protein solution is continuously mixed with chilled water having a temperature below about 15° C. to form protein micellar, which are settled in the settling vessel to provide a protein micellar mass (PMM) while supernatant overflows the vessel. The PMM, when accumulated to a desired degree, may be separated from supernatant and dried. The supernatant may be processed to recover additional oil seed protein isolate.

32 Claims, 1 Drawing Sheet

CONTINUOUS PROCESS FOR PRODUCTION OF OIL SEED PROTEIN ISOLATE

REFERENCE TO RELATED APPLICATIONS

This application is a continuation of U.S. patent application Ser. No. 10/298,678 filed Feb. 14, 2003 now abandoned which, in turn, claims priority under 35 USC 19(e) from U.S. Provisional Patent Application Nos. 60/331,646 filed Nov. 20, 2001 and 60/383,809 filed May 30, 2002.

FIELD OF THE INVENTION

The present invention relates to improved methods for manufacturing oil seed protein isolate.

BACKGROUND TO THE INVENTION

In U.S. Pat. Nos. 5,844,086 and 6,005,076 ("Murray II"), assigned to the assignee hereof and the disclosures of which are incorporated herein by reference, there is described a process for the isolation of protein isolates from oil seed meal having a significant fat content, including canola oil seed meal having such content. The steps involved in this process include solubilizing proteinaceous material from oil seed meal, which also solubilizes fat in the meal and removing fat from the resulting aqueous protein solution. The aqueous protein solution may be separated from the residual oil seed meal before or after the fat removal step. The defatted protein solution then is concentrated to increase the protein concentration while maintaining the ionic strength substantially constant, after which the concentrated protein solution may be subjected to a further fat removal step. The concentrated protein solution then is diluted to cause the formation of a cloud-like mass of highly aggregated protein molecules as discrete protein droplets in micellar form. The protein micelles are allowed to settle to form an aggregated, coalesced, dense amorphous, sticky gluten-like protein isolate mass, termed "protein micellar mass" or PMM, which is separated from residual aqueous phase and dried.

The protein isolate has a protein content, on a dry weight basis, (as determined by Kjeldahl Nx 6.25) of at least about 90 wt %, is substantially undenatured (as determined by differential scanning calorimetry) and has a low residual fat content. The term "protein content" as used herein refers to the quantity of protein in the protein isolate expressed on a dry weight basis. The yield of protein isolate obtained using this procedure, in terms of the proportion of protein extracted from the oil seed meal which is recovered as dried protein isolate was generally less than 40 wt %, typically around 20 wt %.

The procedure described in the aforementioned patents was developed as a modification to and improvement on the procedure for forming a protein isolate from a variety of protein source materials, including oil seeds, as described in U.S. Pat. No. 4,208,323 (Murray IB). The oil seed meals available in 1980, when U.S. Pat. No. 4,208,323 issued, did not have the fat contamination levels of canola oil seed meals, and, as a consequence, the procedure of U.S. Pat. No. 4,208,323 cannot produce from the current oil seed meals processed according to the Murray II process, proteinaceous materials which have more than 90% protein content. There is no description of any specific experiments in U.S. Pat. No. 4,208,303 carried out using rapeseed (canola) meal as the starting material.

U.S. Pat. No. 4,208,323 itself was designed to be an improvement on the process described in U.S. Pat. Nos. 4,169,090 and 4,285,862 (Murray IA) by the introduction of the concentration step prior to dilution to form the PMM. The latter step served to improve the yield of protein isolate from around 20 wt % for the Murray IA process.

In copending U.S. patent application Ser. Nos. 60/288,415 filed May 4, 2001, 60/326,987 filed Oct. 5, 2001, 60/331,066 filed Nov. 7, 2001, 60/333,494 filed Nov. 26, 2001 and 60/374,801 filed Apr. 24, 2002 and filed May 3, 2002, all assigned to the assignee hereof and the disclosure of which are incorporated herein by reference, there is described further improvements on these prior art protein isolation procedures as they apply to oil seeds to obtain improved yields of dried isolated product protein in terms of the proportion of the protein extracted from the oil seeds which is recovered as protein isolate and to obtain protein isolate of high purity, usually at least about 100 wt % at a Kjeldahl nitrogen (N) conversion rate of Nx 6.25. As used herein, protein content is determined on a dry weight basis. The procedure is employed particularly to produce a canola protein isolate.

In the procedure described in the aforementioned U.S. patent application Ser. Nos. 60/288,415, 60/326,987, 60/331,066, 60/333,494, 60/374,801 and 10/137,391, the oil seed meal is extracted with an aqueous food grade salt solution. The resulting protein extract solution, after an initial treatment with colorant adsorbent, if desired, is reduced in volume using ultrafiltration membranes to provide a concentrated protein solution having a protein content in excess of about 200 g/L. The concentrated protein solution then is diluted into cold water, resulting in the formation of a white cloud of protein micelles which are allowed to separate. Following removal of the supernatant, the precipitated, viscous sticky mass (PMM) is dried.

In one embodiment of the process described above and as specifically described in application Ser. Nos. 60/326,987, 60/331,066, 60/333,494, 60/374,801 and 10/137,391, the supernatant from the PMM settling step is processed to remove a protein isolate comprising dried protein from wet PMM and supernatant. This procedure may be effected by initially concentrating the supernatant using ultrafiltration membranes, mixing the concentrated supernatant with the wet PMM and drying the mixture. The resulting canola protein isolate has a high purity of at least about 90 wt %, preferably at least about 100 wt %, protein (Nx 6.25).

In another embodiment of the process described above and specifically described in application Ser. Nos. 60/331,066, 60/333,494, 60/374,801 and 10/137,391, the supernatant from the PMM settling step is processed to recover a protein from the supernatant. This procedure may be effected by initially concentrating the supernatant using ultrafiltration membranes and drying the concentrate. The resulting canola protein isolate has a high purity of at least about 90 wt %, preferably at least about 100 wt %, protein (Nx 6.25).

In copending U.S. patent application Ser. No. 60/339,350 filed Dec. 13, 2001 and Ser. No. 60/391,046 filed Jun. 25, 2002, assigned to the assignee hereof and the disclosure of which is incorporated herein by reference, there is described a procedure in which enhanced levels of protein from canola oil seed meal is achieved by employing a meal which has been desolventized at a temperature of about 100° C. or less. Such meal may be the starting material for the process of this invention.

In copending U.S. patent application Ser. No. 60/401,782 filed Aug. 8, 2002, assigned to the assignee hereof and the disclosures of which are incorporated herein by reference, there is described the recovery of canola protein isolate from the residual meal from solvent extraction of canola oil seed to remove residual quantities of oil, commonly known as "white flake" or less commonly as "marc" meal. Such meal may be used as the starting material for the process of the invention.

SUMMARY OF INVENTION

It has now been found that significant advantages accrue if the procedure of oil seed protein isolate formation is carried out on a continuous basis. The initial protein extraction step can be significantly reduced in time for the same or higher level of protein extraction and significantly higher temperatures can be employed in the extraction step, if the extraction step is carried out in a continuous manner, rather than the batch procedure described in the above-mentioned patents and patent applications. In addition, there is less chance of contamination in a continuous operation, leading to higher product quality, and the process can be carried out in more compact equipment.

The continuous operation disclosed herein may be employed using the concentration and dilution conditions described in the Murray I and II patents but preferably, for the benefits described therein, the continuous operation described herein is preferably effected under the concentration and dilution conditions described in the aforementioned U.S. patent application Ser. Nos. 60/288,415, 60/326,987, 60/331,066, 60/333,494, 60/374,801 and 10/137,391.

In accordance with the present invention, there is provided a process of preparing a protein isolate, which comprises (a) continuously extracting an oil seed meal at a temperature of at least about 5° C. to cause solubilization of protein in the oil seed meal and to form an aqueous protein solution having a pH of about 5 to about 6.8, (b) continuously separating the aqueous protein solution from residual oil seed meal, (c) continuously conveying the aqueous protein solution through a selective membrane operation to increase the protein concentration of the aqueous protein solution to at least about 50 g/L while maintaining the ionic strength substantially constant to provide a concentrated protein solution, (d) continuously mixing the concentrated protein solution with chilled water having a temperature of below about 15° C. to cause the formation of protein micelles in the aqueous phase, (e) continuously flowing the resulting mixture into a settling vessel while permitting supernatant to overflow the vessel, (f) continuously permitting the protein micelles to settle in the settling vessel while continuing to overflow supernatant from the vessel until a desired amount of amorphous, sticky, gelatinous, gluten-like protein micellar mass has accumulated in the settling vessel, and (g) recovering the protein micellar mass from the settling vessel, the protein micellar mass having a protein content of at least about 90 wt %, preferably at least about 100 wt %, as determined by Kjeldahl nitrogen x 6.25.

The protein isolate product in the form of protein micellar mass is described herein as "gluten-like". This description is intended to indicate the appearance and feel of the isolate are similar to those of vital wheat gluten and is not intended to indicate chemical identity to gluten.

In one embodiment of this process, supernatant from the settling step is concentrated, batch-wise, semi-continuously or continuously, and the resulting concentrated supernatant is dried to provide a protein isolate having a protein content of at least about 90 wt % (Nx 6.25) on a dry weight basis.

In another embodiment of this process, supernatant from the settling step is concentrated, batch-wise, semi-continuously or continuously, the resulting concentrated supernatant is mixed with the protein micellar mass prior to drying the same, and the resulting mixture is dried to provide a protein isolate having a protein content of at least about 90 wt % (Nx 6.25) on a dry weight basis.

In a further embodiment of the invention, supernatant from the resulting step is concentrated, batch-wise, semi-continuously continuously, and a portion only of the resulting concentrated supernatant is mixed with at least a portion of the protein micellar mass prior to drying the same to provide other novel protein isolates according to the invention having a protein content of at least about 90 wt % (Nx 6.25) on a dry weight basis.

The protein isolate produced according to the process herein may be used in conventional applications of protein isolates, such as, protein fortification of processed foods, emulsification of oils, body formers in baked goods and foaming agents in products which entrap gases. In addition, the protein isolate may be formed into protein fibers, useful in meat analogs, may be used as an egg white substitute or extender in food products where egg white is used as a binder. The canola protein isolate may be used as nutritional supplements. Other uses of the canola protein isolate are in pets foods, animal feed and in industrial and cosmetic applications and in personal care product.

GENERAL DESCRIPTION OF THE INVENTION

Figure 1:
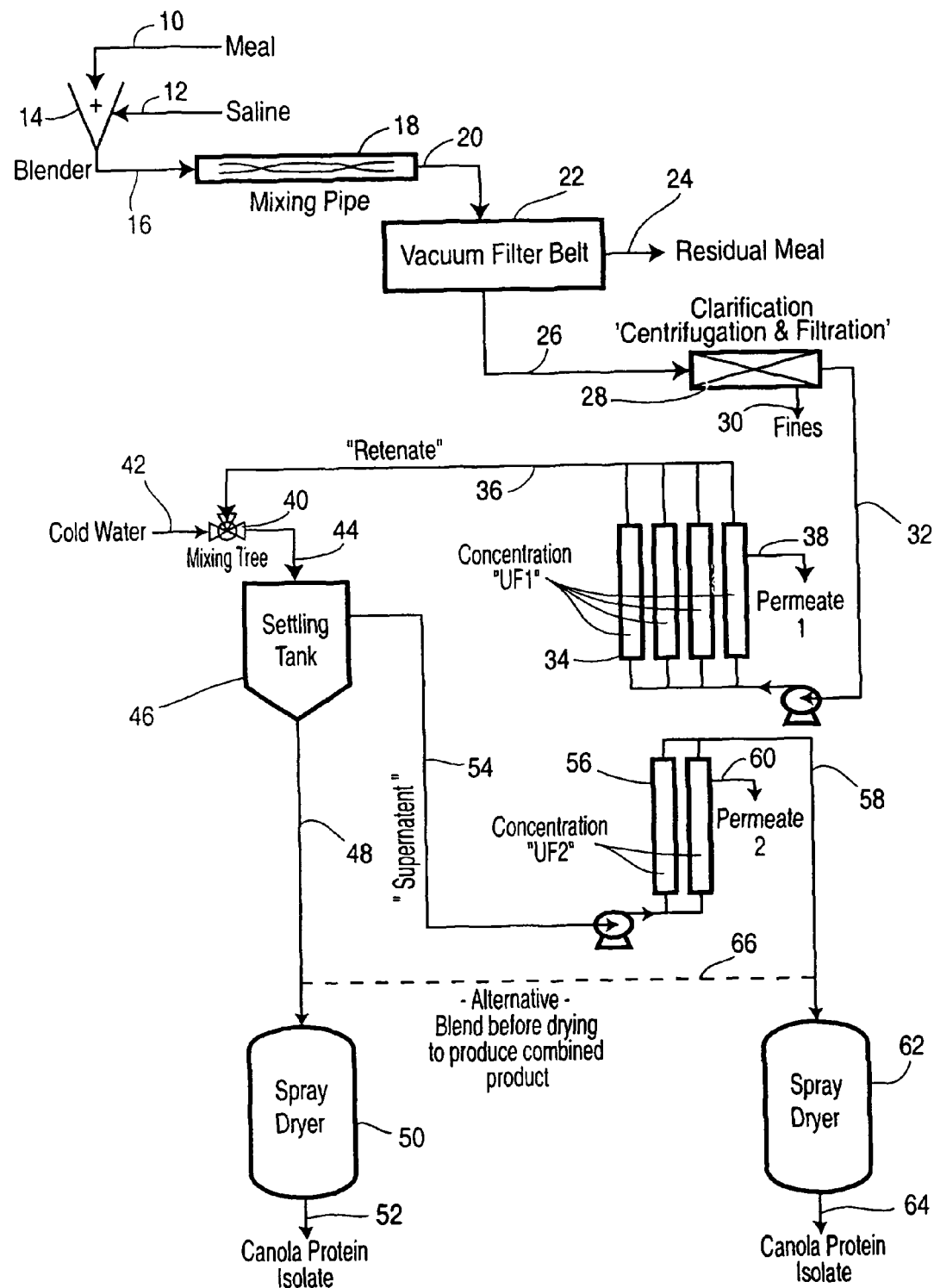
FIG. 1 is a schematic flow sheet of a continuous procedure for producing an oil seed protein isolate in accordance with one embodiment of the invention.

The initial step of the process of this invention involves solubilizing proteinaceous material from oil seed meal, particularly canola meal, although the process may be applied to other oil seed meals, such as soybean, traditional rapeseed, traditional flax, linola, sunflower and mustard oil seed meals. The invention is more particularly described herein with respect to canola seed meal, which may be low temperature desolventized meal.

The proteinaceous material recovered from canola seed meal may be the protein naturally occurring in canola seed or other oil seed or the proteinaceous material may be a protein modified by genetic manipulation but possessing characteristic hydrophobic and polar properties of the natural protein. The canola meal may be any canola meal resulting from the removal of canola oil from canola seed with varying levels of non-denatured protein, resulting, for example, from hot hexane extraction or cold oil extrusion methods. Canola oil seed is also known as rapeseed or oil seed rape.

A salt solution is used in the protein solubilization, and the salt usually is sodium chloride, although other salts suitable for protein extraction, such as, potassium chloride, may be used. The salt solution has an ionic strength of at least about 0.10, preferably at least about 0.15, to enable solubilization of significant quantities of protein to be effected. As the ionic strength of the salt solution increases, the degree of solubilization of protein in the source material initially increases until a maximum value is achieved. Any subsequent increase in ionic strength does not increase the total protein solubilized. The ionic strength of the food grade salt solution which causes maximum protein solubilization varies depending on the salt concerned and the protein source chosen.

In view of the greater degree of dilution required for protein precipitation with increasing ionic strengths, it is usually preferred to utilize an ionic strength value less than about 0.8, and more preferably a value of about 0.15 to about 0.6.

The salt solubilization step is effected rapidly, in a time of generally up to about 10 minutes, preferably to effect the solubilization to extract substantially as much protein from the source material as is practicable, so as to provide an overall high product yield. The solubilization preferably is effected at elevated temperatures, preferably above about 35° C., generally up to about 65° C.

The aqueous salt solution and the oil seed meal have a natural pH of about 5 to about 6.8 to enable the protein isolate to be formed by the micellar route, as described in more detail below. The optimum pH value for maximum yield of protein isolate varies depending on the protein source material chosen.

At and close to the limits of the pH range, protein isolate formation occurs only partly through the micelle route and in lower yields than attainable elsewhere in the pH range. For these reasons, pH values of about 5.3 to about 6.2 are preferred.

The pH of the salt solution may be adjusted to any desired value within the range of about 5 to about 6.8 for use in the extraction step by the use of any convenient acid, usually hydrochloric acid, or alkali, usually sodium hydroxide, as required.

The concentration of protein source material in the salt solution during the solubilization step may vary widely. Typical concentration values are about 5 to about 15% w/v.

The protein extraction step with the aqueous salt solution has the additional effect of solubilizing fats which may be present in the canola meal, which then results in the fats being present in the aqueous phase.

The protein solution resulting from the extraction step generally has a protein concentration of about 5 to about 40 g/L, preferably about 10 to about 30 g/L.

The extraction of the protein from the oil seed meal is carried out in any convenient manner consistent with effecting a continuous extraction of protein from the oil seed meal, such as by passing the mixture of oil seed meal and food grade salt solution through a conduit having a length and at a flow rate for a residence time sufficient to effect the desired extraction in accordance with the above-described parameters.

Alternatively, the extraction procedure may be effected in a stirred tank into which the mixture of oil seed meal and salt solution is continuously fed and from which the aqueous protein solution is continuously removed. In addition, the procedure may be effected in a semi-continuous manner equivalent to continuous wherein a mixture of oil seed meal salt solution is fed into a first stirred vessel in which the extraction is effected to form the aqueous protein solution while aqueous protein solution is continuously fed from a second stirred vessel to the residual meal separation step described below. When the aqueous protein solution has been formed in the first vessel and the second vessel has been depleted of aqueous protein solution, the first vessel then becomes the first vessel and vice versa.

The aqueous phase resulting from the extraction step then may be separated from the residual canola meal in any convenient manner, such as by employing vacuum filtration, followed by centrifugation and/or filtration to remove residual meal. The separated residual meal may be dried for disposal.

The colour of the final protein isolate can be improved in terms of light colour and less intense yellow by the mixing of powdered activated carbon or other pigment adsorbing agent with the separated aqueous protein solution and subsequently removing the adsorbent, conveniently by filtration, to provide a protein solution. Diafiltration of the separated aqueous protein solution also may be used for pigment removal.

Such pigment removal step may be carried out under any convenient conditions, generally at the ambient temperature of the separated aqueous protein solution, employing any suitable pigment adsorbing agent. For powdered activated carbon, an amount of about 0.025 to about 5 w/v, preferably about 0.05 to about 2 w/v, is employed.

Where the canola seed meal contains significant quantities of fat, as described in U.S. Pat. Nos. 5,844,006 and 6,005,076, assigned to the assignee hereof and the disclosures of which are incorporated herein by reference, then the defatting steps described therein on the separated aqueous protein solution and on the concentrated aqueous protein solution may be effected. When the colour improvement step is carried out, such step may be effected after the first defatting step.

As an alternative to extracting the oil seed meal with an aqueous salt solution, such extraction may be made using water alone, although the utilization of water alone tends to extract less protein from the oil seed meal than the aqueous salt solution. Where such alternative is employed, then the salt, in the concentrations discussed above, is added to the protein solution after separation from the residual oil seed meal in order to maintain the protein in solution during the concentration step. When a colour removal step and/or a first fat removal step is carried out, the salt generally is added after completion of such operations.

Another alternative procedure is to extract the oil seed meal with the salt solution at a relatively high pH value above about pH 6.8, generally up to about 9.9. The pH of the salt solution, may be adjusted in pH to the alkaline value by the use of any convenient alkali, such as aqueous sodium hydroxide solution. Alternatively, the oil seed meal may be extracted with the salt solution at a relatively low pH below about pH 5, generally down to about pH 3. The pH of the salt solution may be adjusted in pH to the acidic value by the use of any convenient acid, such as hydrochloric acid. Where such alternative are employed, the aqueous phase resulting from the oil seed meal extraction step then is separated from the residual canola meal, in any convenient manner, such as by employing vacuum filtration, followed by centrifugation and/or filtration to remove residual meal. The separated residual meal may be dried for disposal.

The aqueous protein solution resulting from the high or low pH extraction step then is pH adjusted to the range of about 5 to about 6.8, preferably about 5.3 to about 6.2, as discussed above, prior to further processing as discussed below. Such pH adjustment may be effected using any convenient acid, such as hydrochloric acid, or alkali, such as sodium hydroxide, as appropriate.

The aqueous protein solution then is concentrated to increase the protein concentration thereof while maintaining the ionic strength thereof substantially constant. Such concentration may be effected to provide a concentrated protein solution having a protein concentration of at least about 50 g/L. In order to obtain an improved yield of protein isolate, as described in the aforementioned U.S. patent application Ser. Nos. 60/288,415, 60/326,987, 60/331,066, 60/333,494, 60/374,801 and 10/137,391, such concentration is effected preferably to provide a concentrated protein solution having a protein concentration of at least about 200 g/L, more preferably at least about 250 g/L.

The concentration step may be effected in any convenient manner consistent with a continuous operation, such as by employing any convenient selective membrane technique, such as ultrafiltration, using membranes, such as hollow-fibre membranes or spiral-wound membranes, with a suitable molecular weight cut-off, such as from about 3000 to about 50,000 daltons, having regard to differing membrane materials and configurations, and dimensioned to permit the desired degree of concentration of the aqueous protein solution as the aqueous protein solution passes through the membranes.

The concentration step may be effected at any convenient temperature, generally about 20° to about 60° C., and for the period of time to effect the desired degree of concentration. The temperature and other conditions used to some degree depend upon the membrane equipment used to effect the concentration and the desired protein concentration of the solution.

As is well known, ultrafiltration and similar selective membrane techniques permit low molecular weight species to pass therethrough while preventing high molecular weight species from so doing. The low molecular weight species include not only the ionic species of the food grade salt but also low molecular weight materials extracted from the source material, such as, carbohydrates, pigments and anti-nutritional factors, as well as any low molecular weight forms of the protein. The molecular weight cut-off of the membrane is usually chosen to ensure retention of a significant proportion of the protein in the solution, while permitting contaminants to pass through having regard to the different membrane materials and configurations.

When the concentration is effected to provide a concentrated aqueous protein solution having a protein content of at least about 200 g/L, preferably at least about 250 g/L and depending on the temperature employed in the concentration step, the concentrated protein solution may be warmed to a temperature of about 20° to about 60° C., preferably about 25° to about 35° C., to decrease the viscosity of the concentrated protein solution to facilitate the subsequent dilution step and micelle formation. The concentrated protein solution should not be heated beyond a temperature above which the temperature of the concentrated protein solution does not permit micelle formation on dilution into chilled water.

The concentrated protein solution may be subject to a further defatting operation, if required, as described in the aforementioned U.S. Pat. Nos. 5,844,006 and 6,005,076.

The concentrated protein solution resulting from the concentration step and optional defatting step then is diluted to effect micelle formation by mixing the concentrated protein solution with chilled water having the volume required to achieve degree of dilution desired. Depending on the proportion of protein desired to be obtained by the micelle route and the proportion from the supernatant, the degrees of dilution may be varied. With higher dilution levels, in general, a greater proportion of the canola protein remains in the aqueous phase. When it is desired to provide the greatest proportion of the protein by the micelle route, the concentrated protein solution is diluted by less than about 15 fold, more preferably about 10 fold or less.

The dilution operation may be carried out by continuously passing the concentrated protein solution to one inlet of a T-shaped pipe while the diluting water is fed to the other inlet of the T-shaped pipe, permitting mixing in the pipe. The diluting water is fed into the T-shaped pipe at a rate sufficient to achieve the desired degree of dilution. The diluting water has a temperature of less than about 15° C., generally about 3° to about 15° C., preferably less than about 10° C., since improved yields of protein isolate in the form of protein micelles are attained with these colder temperatures at the dilution factors used.

The mixing of the concentrated protein solution and the diluting water in the pipe initiates the formation of protein micelles and the mixture is continuously fed from the outlet from the T-shaped pipe into a settling vessel, from which, when full, supernatant is permitted to overflow. The settling vessel may be initially charged full with chilled water which gradually is displaced by the inflowing mixture from the exit to the pipe.

The mixture is fed into the body of liquid in the settling vessel in a manner which minimizes turbulence within the body of liquid to permit proper settling of the micelles. To achieve this result, the mixture usually is fed from the outlet to the T-shaped pipe below the surface of the body of liquid in the settling vessel. In addition, the outlet may be configured and structured so that the liquid flows out of the pipe in a radial direction in the upper levels of the settling vessel.

The protein micelles are allowed to settle in the settling vessel to form an aggregated, coalesced, dense amorphous gluten-like protein micellar mass (PMM) and the procedure is continued until a desired quantity of the PMM has accumulated in the bottom of the settling vessel, whereupon the accumulated PMM is removed from the settling vessel. The protein micellar mass may be subjected to centrifugation to decrease the liquid content of the mass prior to removal of accumulated PMM from the settling vessel. Centrifugation may decrease the moisture content of the protein micellar mass from about 70 wt % to about 95 wt % to a value of generally about 50% by weight to about 80 wt % of the total micellar mass. Decreasing the moisture content of the protein micellar mass in this way also decreases the occluded salt content of the protein micellar mass, and hence the salt content of dried isolate. Alternatively, the settling step may be effected under continuous centrifugation.

The recovered PMM may be used in wet form or may be dried, by any convenient technique, such as spray drying, freeze drying or vacuum drum drying, to a dry form. The dry PMM has a high protein content of at least about 90 wt %, usually in excess of about 100 wt % protein (calculated as Kjeldahl Nx 6.25), and is substantially undenatured (as determined by differential scanning calorimetry). The dry PMM isolated from fatty oil seed meal also has a low residual fat content, when the procedure of the aforementioned U.S. Pat. Nos. 5,844,086 and 6,005,026 is employed, which may be below about 1 wt %.

As specifically described in the aforementioned U.S. patent application Ser. Nos. 60/331,066, 6/333,494, 60/374, 801 and 10/137,391, the supernatant from the PMM formation step may be processed to recover further protein therefrom. Such procedure may include an initial concentration of the supernatant. Such concentration is effected using any convenient selective membrane technique, such as ultrafiltration, using membranes with a suitable molecular weight cut-off permitting low molecular weight species, including salt and other non-proteinaceous low molecular weight material extracted from the protein source material, to pass through the membrane, while retaining canola protein in the solution. Ultrafiltration membranes having a molecular weight cut-off of about 3000 to about 10,000, having regard to differing membrane materials and configuration, may be used. The concentration preferably is effected continuously on the continuously overflowing supernatant, although a batch procedure on collected volumes of the overflowing supernatant may be employed, if desired. In such continuous operation, the membranes are dimensioned to permit the desired degree of concentration of the supernatant as the supernatant passes through the membranes.

Concentration of the supernatant in this way also reduces the volume of liquid required to be dried to recover the protein isolate and hence the energy required for drying. The supernatant generally is concentrated to a protein concentration of about 100 to about 400 g/L, preferably about 200 to about 300 g/L, prior to drying.

The concentrated supernatant may be dried in any convenient manner, such as by spray drying, freeze drying or vacuum drum drying, to a dry form, to provide a further canola protein isolate having a protein content of at least about 90 wt %, preferably at least about 100 wt %, (Nx 6.25), and which is substantially undenatured (as determined by differential scanning calorimetry).

Alternatively, as described in the aforementioned U.S. patent application Ser. Nos. 60/326,987, 60/331,066, 60/333,494, 60/374,801 and 10/137,391, the concentrated supernatant may be mixed with the wet PMM and the resulting mixture dried, to provide a further canola protein isolate having protein content of at least about 90 wt %, preferably at least about 100 wt % (Nx 6.25) and which is substantially undenatured (as determined by differential scanning calorimetry).

In another alternative procedure, where a portion only of the concentrated supernatant is mixed with a part only of the PMM and the resulting mixture dried, the remainder of the concentrated supernatant may be dried as may any of the remainder of the PMM. Further, dried PMM and dried supernatant also may be dry mixed in any desired relative proportions, as discussed above.

DESCRIPTION OF PREFERRED EMBODIMENT

Referring to FIG. 1, there is illustrated schematically a flow sheet of one embodiment to the invention. Canola oil seed meal and aqueous extraction medium are fed by lines 10 and 12 respectively to a blender 14 wherein the oil seed meal and aqueous extraction medium are mixed and the mixture is passed by line 16 to a mixing pipe 18. In the mixing pipe 18, the oil seed meal is extracted and an aqueous protein solution is formed. The slurry of aqueous protein solution and residual oilseed meal is passed by line 20 to a vacuum filter belt 22 for separation of the residual oil seed meal which is removed by line 24. The aqueous protein solution then is passed by line 26 to a clarification operation 28 wherein the aqueous protein solution is centrifuged and filtered to remove fines, which are recovered by line 30.

The clarified aqueous protein solution is pumped by line 32 through ultrafiltration membranes 34 sized to provide the desired degree of concentration of the aqueous protein solution to produce a concentrated protein solution as the retentate in line 36 with the permeate being recovered by line 38. The concentrated protein solution is passed into the inlet of a mixing tee 40, with cold water being fed thereto by line 42 in a volume sufficient to achieve the desired degree of dilution. The resulting solution is fed by line 44 to a settling tank 46 to permit the protein micellar mass to settle. Protein micellar mass settled in the settling vessel 46 is removed by line 48 from time to time and passed through a spray dryer 50 to provide dry canola protein isolate 52.

Supernatant from the settling tank is removed by line 54 and pumped through ultrafiltration membranes 52 to produce a concentrated protein solution as the retentate in line 58 with the permeate being removed by line 60. The concentrated protein solution is passed through a spray dryer 62 to provide further dry canola protein isolate 64.

As an alternative, the concentrated protein solution in line 58 may be passed by line 66 to mix with the protein micellar mass before the mixture then is dried in spray dryer 50.

EXAMPLES

Example 1

This Example illustrates a continuous process for the production of canola protein isolate in accordance with one embodiment of the invention.

200 g of canola meal was added to 1350 ml (15% w/v) of a 0.15M sodium chloride solution at 50° C. The resulting mixture was passed through tubing of a sufficient length to give 5 minutes total residence time of the mixture in the tubing. Analysis of the extract leaving the tubing showed a protein content of 20.5 g/L. By way of contrast, in a batch mode, salt solubilization (0.15 M NaCl) of a 15% w/v solution of canola meal achieved a protein content of 18.3 g/l after 30 minutes of mixing at 24° C. (Run BW-AH014-H29-01A).

8 litres of a concentrated retentate with a protein content of 296 g/L was prepared by a batch procedure as described in Example 2 (see BW-AH014-H29-01A). The concentrated retentate, at a temperature of 30° C., was pumped into one inlet of a T-shaped connection pipe at a rate of 64 ml/minute to mix with 4° C. water pumped into the other inlet of the T-shaped connection pipe at a rate to provide a dilution ratio of 1:10. The T-shaped connector served as a device to mix the two streams and to cause the formation of a white cloud of protein micelles. The mixture then passed from the outlet from the T-shaped connection pipe into a 50 litre settling vessel filled with 4° C. water where the mixture exited the pipe through a outlet designed to minimize turbulence in the settling vessel. Supernatant was removed from the top of the settling vessel maintaining the vessel at a constant volume. The system ran for two hours.

As the retentate/water mixture flowed into the settling vessel a boundary layer began to form between micelles and the supernatant. This layer moved upwards in the vessel for the first hour after which it began to settle. At the same time, a layer of precipitated, viscous sticky mass (PMM) was visible at the bottom of the settling vessel. As the run progressed, the PMM layer grew steadily in volume. The boundary layer between the settling micelles and the supernatant steadied at a level approximately even with the retentate/water outlet. The supernatant as it exited the settling vessel was clear and there were no visible micelles in the supernatant being removed.

The PMM removed from the bottom of the vessel following the settling period had a solids content of 29.8 wt % and represented 49 wt % of the protein in the retentate.

By way of the contrast, in a batch mode, 40 litres of concentrated retentate with a protein content of 283 g/L at a temperature of 30° C. was diluted 1:10 into 4° C. tap water and the micelles were allowed to settle for 1 hour. The PMM recovered from the bottom of the vessel had a solids content of 36.2 wt % and represented 42 wt % of the protein in the retentate (Run BW-AH014-I05-01A) (see Example 2).

Example 2

This Example provides details of the batch procedures described in the preceding Example.

"a" kg of concentrated canola meal was added to "b" L of 0.15 M NaCl solution at ambient temperature and agitated for "c" minutes to provide an aqueous protein solution having a protein content of "d" g/L. The residual canola meal was removed and washed on a vacuum filter belt. The resulting protein solution was clarified by centrifugation to produce a clarified protein solution having a protein content of "e" g/L.

The protein extract solution was reduced in volume on an ultrafiltration system using membranes having a molecular weight cut-off of 3000 daltons. The resulting concentrated protein solution had a protein content of "f" g/L. The concentrated solution at "g" ° C. was diluted 1:10 into 4° C. tap water. A white cloud formed immediately and was allowed to settle. The upper diluting water was removed and the precipitated, viscous, sticky mass was dried. The product was given designation "h".

The specific parameters "a" to "h" for the different samples of protein product are set forth in the following Table I:

TABLE I

| H | a | b | c | d | e | f | g |
|---|---|---|---|---|---|---|---|
| BW-AH014-H29-01A | 1200 | 8000 | 30 | 18.3 | 14.7 | 296 | (1) |
| BW-AH014-I05-01A | 1200 | 8000 | 30 | 19.0 | 14.2 | 283 | 36.8 |

(1) not available

Example 3

This Example illustrates the application of the continuous extraction stage of the continuous process to mustard, non-GMO canola, high euricic acid rapeseed (H.E.A.R.), white flake canola meal and cold pressed canola meal.

Oil seed meals were added to separate 500 ml aliquots of 55° C., 0.15 M NaCl solution to provide mixtures having the following concentrations:
mustard, high euricic acid rapeseed and a non-GMO canola: 15% w/v
a white flake and cold pressed canola meal: 10% w/v The mixtures were pumped through a pipe having a length permitting a 5 minute extraction time in the pipe. Samples were analyzed for protein content as soon as exiting the pipe.

The results obtained are set forth in the following Table II:

TABLE II

| Oilseed Meal | Protein content of extract |
|---|---|
| Mustard | 27.3 mg/ml |
| H.E.A.R. | 12.0 mg/ml |
| Non-GMO Canola | 10.7 mg/ml |
| White flake | 23.0 mg/ml |
| Cold pressed Canola | 21.1 mg/ml |

Example 4

This Example illustrates the application of the continuous dilution stage of the continuous process to mustard, non-GMO canola, high euricic acid rapeseed, white flake canola meal and cold pressed canola meal.

Extraction of oil seed meals were performed in 0.15 M NaCl solution at room temperature with a 30-minute mixing period for each oil seed meal. The seed concentrations were 10% w/v for white flake and cold pressed canola meals and 15% w/v for H.E.A.R., non-GMO canola meal and mustard meal. Following the 30-minute mixing period, the solid material was separated from the extraction protein solution by centrifugation at 10,000×g for 10 minutes. The protein solutions were further clarified by filtering through Whatman #4 filter papers on a vacuum filter apparatus.

Each clarified was concentrated on a Amicon mini stirred-cell concentration system using membranes of MWCO sufficient to retain the soluble protein while allowing water and contaminating small molecular weight material to pass through the permeate. Each protein solution was concentrated to 200 mg/ml or greater.

Following concentration, the retentates were diluted in a continuous manner by using two peristaltic pumps and a t-shaped connector. The pump speeds were adjusted to allow the first pump to move fluid at a rate 10 times faster than the first pump, to provide a dilution ratio of retentate to water of 1:10. The pumps were started simultaneously and the retentates and water were pumped into a common line through the t-shaped connector where they were mixed and micelle formation commenced.

The resulting solutions were then passed into settling tanks where the precipitates were allowed to settle. Pellets of settled PMM were collected and freeze dried to calculate yield and protein content of each PMM formed. The results obtained for each seed are set forth in Tables III and IV below:

TABLE III

| | EXTRACTS | | |
|---|---|---|---|
| Oil Seed Meal | Protein Content | Volume of Extract | Quantity of Protein |
| H.E.A.R. | 11.7 mg/ml | 800 ml | 9.36 g |
| Mustard | 31.6 mg/ml | 600 ml | 19.0 g |
| Non-GMO canola | 6.9 mg/ml | 1000 ml | 6.9 g |
| White flake canola | 18.0 mg/ml | 900 ml | 16.2 g |
| Cold press canola | 16.4 mg/ml | 1000 ml | 16.4 g |

TABLE IV

| | PMM | | |
|---|---|---|---|
| Oil Seed Meal | Weight | Protein content[1] | Yield[2] |
| H.E.A.R. | 3.71 g | 107 wt. % | 40 wt. % |
| Mustard | 8.54 g | 101 wt. % | 45 wt. % |
| Non-GMO canola | 2.92 g | 103 wt. % | 42 wt. % |
| White Flake canola | 7.1 g | 105 wt. % | 44 wt. % |
| Cold press canola | 6.94 g | 100 wt. % | 42 wt. % |

Notes:
[1] Protein content was determined as Kjeldahl nitrogen × 6.25. All PMM products formed were protein isolates.
[2] Yield was determined as the proportion of the protein extracted which was recovered as PMM.

SUMMARY OF DISCLOSURE

In summary of this disclosure, the present invention provides a continuous process for the production of oil seed protein isolate. Modifications are possible within the scope of the invention.

What we claim is:

1. A process of preparing a canola protein isolate, which comprises:
(a) continuously extracting a canola oil seed meal to cause solubilization of canola protein in said canola oil seed meal and to form an aqueous canola protein solution having a pH of about 5 to about 6.8, said continuous extraction step being effected by:
(i) continuously mixing the canola oil seed meal with an aqueous salt solution having an ionic strength of at least about 0.10 and a pH of about 5 to about 6.8 at a temperature of above about 35° C. to about 65° C., and (ii) continuously conveying said mixture through a pipe while extracting protein from the canola oil seed meal to form an aqueous canola protein solution having a protein content of about 5 to about 40 g/L in a period of time up to about 10 minutes, (b) continuously separating said aqueous canola protein solution from residual oil seed meal, (c) continuously conveying said aqueous canola protein solution through a selective membrane operation to increase the protein concentration of said aqueous canola protein solution to at least about 200 g/L while maintaining the ionic strength substantially constant to provide a concentrated canola protein solution, (d) continuously mixing said concentrated canola protein solution with chilled water having a temperature of below about 15° C. to cause the formation of canola protein micelles in the aqueous phase, (e) continuously flowing the resulting mixture into a settling vessel while permitting supernatant to overflow the vessel, (f) continuously permitting said canola protein micelles to settle in the settling vessel while continuing to overflow supernatant from the vessel until a desired amount of amorphous, sticky, gelatinous, gluten-like canola protein micellar mass has accumulated in said settling vessel, and (g) recovering said canals protein micellar mass from the settling vessel, said canola protein micellar mass having a protein content, on a dry weight basis, of at least about 100 wt % as determined by Kjeldahl nitrogen x 6.25, wherein said supernatant is processed, on a batch, semi-continuous or continuous basis, to recover additional quantities of canola protein isolate therefrom.

2. The process of claim 1 wherein said salt solution has an ionic strength of about 0.15 to about 0.8.

3. The process of claim 1 wherein the salt solution has a pH of about 5.3 to about 6.2.

4. The process of claim 1 wherein the concentration of canola oil seed meal in said aqueous salt solution in said mixing step is about 5 to about 15% w/v.

5. The process of claim 1 wherein said aqueous protein solution has a protein content of about 10 to about 30 g/L.

6. The process of claim 1 wherein said extraction step is effected using an aqueous salt solution having an ionic strength of at least about 0.10 and a pH of about 3 to about 5 or about 6.8 to about 9.9 and, following said separation of the aqueous canola protein solution from residual oil seed meal, the pH of the aqueous canola protein solution is adjusted to a pH of about 5 to about 6.8.

7. The process of claim 6 wherein said salt solution has an ionic strength of about 0.15 to about 0.6.

8. The process of claim 6 wherein the pH of the aqueous canola protein solution is adjusted to a pH of about 5.3 to about 6.2.

9. The process of claim 1 wherein, following said separation of the aqueous canola protein solution from the residual canola seed meal, the aqueous canals protein solution is subjected continuously to a pigment removal step.

10. The process of claim 9 wherein said pigment removal step is effected by diafiltration of the aqueous canola protein solution.

11. The process of claim 9 wherein said pigment removal step is effected by continuously mixing a pigment adsorbing agent with the aqueous canola protein solution and subsequently continuously removing the pigment adsorbing agent from the aqueous canola protein isolation.

12. The process of claim 11 wherein the pigment adsorbing agent is powdered activated carbon.

13. The process of claim 1 wherein said canola oil seed meal is continuously extracted by water and, subsequent thereto, salt is continuously added to the resulting aqueous canola protein solution to provide an aqueous canola protein solution having an ionic strength of at least about 0.10.

14. The process of claim 1 wherein said concentration step is effected to produce a concentrated canola protein solution having a canola protein content of at least about 250 g/L.

15. The process of claim 1 wherein said concentrated protein solution is warmed to a temperature of at least about 20° C. to decrease the viscosity of the concentrated canola protein solution but not beyond a temperature above which the temperature of the concentrated canola protein solution does not permit micelle formation.

16. The process of claim 15 wherein said concentrated canola protein solution is warmed to a temperature of about 250° to about 40° C.

17. The process of claim 1 wherein said concentrated canola protein solution is continuously mixed with said chilled water to provide a dilution of the concentrated canola protein solution by about 15 fold or less.

18. The process of claim 17 wherein said chilled water has a temperature of less than about 10° C.

19. The process of claim 18 wherein said dilution is by about 10 fold or less.

20. The process of claim 1 wherein said recovered canola protein micellar mass is dried to a proteinaceous powder.

21. The process of claim 1 wherein said canola oil seed meal is cold pressed canola oil seed meal.

22. The process of claim 1 wherein said canola oil seed meal is white flake.

23. The process of claim 1 wherein said canola oil seed meal is derived from a non-genetically modified canola oil seed.

24. The process of claim 1 wherein said canola oil seed meal is low temperature desolventized canola oil seed meal.

25. The process of claim 1 wherein said additional quantities of protein solution are recovered from the overflowing supernatant by concentrating the supernatant to a protein concentration of about 100 to about 400 g/L and drying the concentrated supernatant to produce a protein isolate having a protein content of at least about 90 wt % (Nx 6.25) and which is substantially undenatured (as determined by differential scanning calorimetry).

26. The process of claim 25 wherein said supernatant is concentrated to a protein concentration of about 200 to about 300 g/L.

27. The process of claim 1 wherein said additional quantities of protein isolate was recovered from the overflowing supernatant by concentrating the supernatant to a protein concentration of about 100 to about 400 g/L, mixing the concentrated supernatant with the recovered protein micellar mass, and drying the mixture to obtain a protein while having a protein content of at least about 90 wt % (Nx 6.25) and which is substantially undenatured (as determined by differential scanning calorimetry).

28. The process of claim 27 wherein said supernatant is concentrated to a protein concentration of about 200 to about 300 g/L.

29. The process of claim 1 wherein said additional quantities of protein isolate are recovered from the supernatant by concentrating the overflowing supernatant to a protein concentration of about 100 to about 400 g/L, mixing a portion of the concentrated supernatant with at least a portion of the recovered protein micellar mass, and drying the resulting mixture, and optionally drying the remainder of the concentrated supernatant and the remainder of the recovered protein micellar mass.

30. The process of claim 29 wherein said supernatant is concentrated to a protein concentration of about 200 to about 300 g/L.

31. The process of claim 25 wherein said additional quantities of canola protein isolate have a protein content of at least about 100 wt % (Nx 8.25).

32. The process of claim 27 wherein said additional quantities of canola protein isolate have a protein content of at least about 100 wt % (Nx 6.25).

* * * * *